United States Patent [19]

Bobek et al.

[11] 4,230,698

[45] Oct. 28, 1980

[54] 2-SUBSTITUTED ARABINOFURANOSYL NUCLEOSIDES AND NUCLEOTIDES

[75] Inventors: Miroslav V. Bobek, Williamsville; Alexander Bloch, Athol Springs; Yung-Chi Cheng, Buffalo, all of N.Y.

[73] Assignee: Research Corporation, New York, N.Y.

[21] Appl. No.: 905,529

[22] Filed: May 12, 1978

[51] Int. Cl.$^3$ .................. A61K 31/70; C07H 17/00; C07H 15/12; C07H 17/00

[52] U.S. Cl. .................. 424/180; 536/23; 536/24; 536/27; 536/28; 536/29

[58] Field of Search .............. 536/23, 24, 27, 28, 536/29; 424/180

[56] References Cited

U.S. PATENT DOCUMENTS

| | | | |
|---|---|---|---|
| 3,116,282 | 12/1963 | Hunter | 536/23 |
| 3,501,456 | 3/1970 | Shen et al. | 536/23 |
| 3,755,295 | 8/1973 | Verheyden et al. | 536/23 |
| 3,809,689 | 5/1974 | Damadaran et al. | 536/24 |
| 3,987,030 | 10/1976 | Suzuki et al. | 536/24 |

FOREIGN PATENT DOCUMENTS 1070413 6/1967 United Kingdom.

OTHER PUBLICATIONS

Reist, E., et al. J. Organic Chemistry, vol. 32, 2538–2541 (1967).
Unger et al., Tetrahedron Letters, No. 50, pp. 4383–4384 (1977).

Primary Examiner—Johnnie R. Brown
Assistant Examiner—Blondel Hazel
Attorney, Agent, or Firm—Sutherland, Asbill & Brennan

[57] ABSTRACT

Novel arabinofuranosyl nucleosides and nucleotides having 2'-azido, 2'-amino, or 2'-hydrocarbylamino substituents, which have antitumor, antiviral, and antimicrobial properties, are prepared by condensation of a pyrimidine, purine, or 1,3-oxazine base with an acylated 2-azido-2-deoxyarabinofuranosyl halide, followed by deblocking and catalytic hydrogenation, where appropriate, to convert the 2'-azido group to a 2'-amino group and, if desired, alkylation or the like to convert the 2'-amino group to a 2'-hydrocarbylamino group.

12 Claims, No Drawings

2-SUBSTITUTED ARABINOFURANOSYL NUCLEOSIDES AND NUCLEOTIDES

Support for the work leading to this invention was provided by grants from the American Cancer Society (Grant No. CH-55A, B) and The National Institutes of Health/National Cancer Institute (Grants Nos. CA-12585 and 18499).

This invention concerns novel arabinofuranosyl nucleosides and nucleotides which have useful antitumor, antiviral, and antimicrobial activities, processes of preparing these nucleosides and nucleotides, and pharmaceutical compositions containing them. More particularly, the invention is concerned with 2'-deoxyarabinofuranosyl nucleosides and nucleotides having an azido, amino, or hydrocarbylamino group on the 2' carbon atom.

Various nucleic acid derivatives have been found to possess antitumor activity. Frequently, however, they are susceptible to deamination (and, therefore, deactivation) by deaminase enzymes found in mammals. This limits their effectiveness in antitumor therapy, for example requiring frequent, repeated administrations by injection, e.g., intravenous infusion, and/or administration in combination with a compatible inhibitor which is active against deaminase enzymes. The need for an effective, deaminase resistant antitumor agent is generally recognized. In searching for such an agent we have developed a new family of arabinofuranosyl nucleosides and nucleotides which exhibit useful antitumor, antiviral, and antimicrobial properties, and which come within the formula

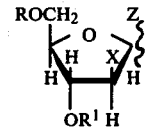

wherein Z is a pyrimidinyl-1, purinyl-9, or 1,3-oxazinyl-3 moiety and X is selected from the group consisting of amino, azido, hydrocarbylamino (e.g., alkylamino) of 1 to 7 carbon atoms,

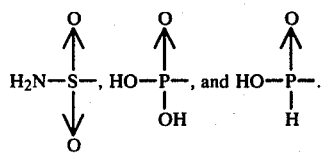

In addition, some of the members having antitumor potency exhibit the desired resistance to enzymatic deamination.

Preparation of the 2'-azido nucleosides of the present invention may be by (a) blocking the labile hydrogen sites on a pyrimidine, purine, or 1,3-oxazine base by silylation or alkoxylation and (b) condensing the blocked base with a 2-azido-2-deoxyarabinofuranosyl halide of the formula

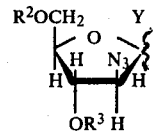

wherein each of $R^2$ and $R^3$ is hydrocarbylcarbonyl of 2 to 12 or 20 carbon atoms and Y is chloro or bromo, or alkanoyl, or acyloxy to obtain nucleosides of the formula

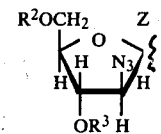

wherein Z is a pyrimidinyl-1, purinyl-9, or 1,3-oxazinyl-3 moiety.

The pyrimidine, purine, or 1,3-oxazine base can be substituted or unsubstituted and may be acylated with hydrolyzable acyl groups.

A preferred group of pyrimidine bases are those corresponding to the formula

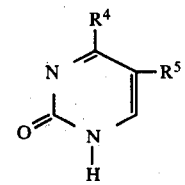

wherein $R^4$ is amino, hydroxy, thio, hydroxylamino, alkylamino, arylamino, or aralkylamino, and $R^5$ is fluoro, bromo, chloro, hydrogen, iodo, mercapto, nitro, nitrilo, thiocyanato, alkyl, alkenyl, or alkynyl.

A preferred group of purine bases are those corresponding to the formula

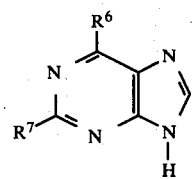

wherein $R^6$ is amino, hydrogen, hydroxylamino, thio, chloro, alkylamino, arylamino, or aralkylamino, and $R^7$ is hydrogen, oxo, chloro, fluoro, amino, nitro, thio, or hydroxyalkyl.

Suitable examples of pyrimidine bases include cytosine, uracil, thymine, 5-fluorouracil, 5-azauracil, 5-azacytosine, dihydro-5-azauracil, dihydro-5-azacytosine, 6-azauracil, 6-azacytosine, 3-deazauracil, and 3-deazacytosine. Examples of suitable purine bases include adenine, guanine, 6-chloropurine, hypoxanthine, and xanthine, as well as the 1-deaza, 2-aza, 3-deaza, 7-deaza, 8-aza, 2,8-diaza, 7-deaza-8-aza, and 9-deaza derivatives of those compounds.

Hydrolyzable acyl groups which may be present on the heterocyclic base include acetyl, propionyl, butyryl, valeryl, isovaleryl, hexanoyl, heptanoyl, octanoyl, nonanoyl, undecanoyl, lauroyl, benzoyl, phenylacetyl, phenylpropionyl, o-, m-, and p-methylbenzoyl, β-cyclopentylpropionyl, dihydrocinnamoyl, and the like.

Silylation or alkoxylation of the labile hydrogen sites on the heterocyclic base can be accomplished by known methods. Silylation, for example as described in British Patent Specification No. 1,070,413, can be used. The procedure generally involves reacting the labile hydrogen-containing base at about room temperature with a tri(lower)alkyl-chlorosilane in the presence of a tertiary amine in an anhydrous organic solvent such as benzene, toluene, xylene, and dioxane. Suitable tertiary amines include tri(lower)alkyl amines such as trimethylamine, triethylamine, and tripropylamine. Alternatively, silylation can be effected by suspending the base in anhydrous hexa(lower)alkyldisilazane and heating to reflux.

Preparation of the 2-azido-2-deoxy-arabinofuranosyl halide can be by a multi-step synthesis involving (a) acylating (e.g. benzoylating) 1,2-O-isopropylidene-3-azido-3-deoxy-α-D-glucofuranose (described by Meyer zu Reckendorf in *Chemische Berichte*, vol. 101, p. 3802 (1968)) to obtain 1,2-O-isopropylidene-6-O-acyl-3-azido-3-deoxy-α-D-glucofuranose of the formula

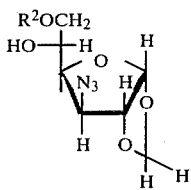

wherein $R^2$ is hydrocarbylcarbonyl of 2 to 12 carbon atoms, (b) hydrolyzing the product of step (a) to obtain 6-O-acyl-3-azido-3-deoxy-D-glucofuranose of the formula

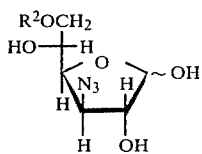

(c) oxidizing and hydrolyzing the product of step (b) to obtain 5-O-acyl-2-azido-2-deoxy-D-arabinofuranose of the formula

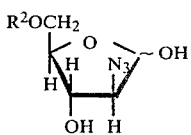

(d) acylating (e.g. acetylating) the product of step (c) to obtain 1,3-di-O-acyl-5-O-acyl-2-azido-2-deoxyarabinofuranose of the formula

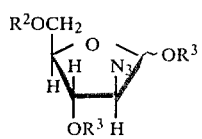

wherein $R^3$ is hydrocarbylcarbonyl of 2 to 12 carbon atoms, and (e) halogenating the product of step (d) to obtain the 2-azido-2-deoxyarabinofuranosyl halide.

The same hydrolyzable acyl groups described earlier herein can generally be used in the above synthesis of the 2-azido-2-deoxyarabinofuranosyl halide. Steps (a) and (d) of that synthesis can be accomplished by conventional acylation techniques. The step (b) hydrolysis can be performed by contacting an aqueous solution of the compound with a cation exchange resin. Oxidation and hydrolysis (step (c)) can be achieved by reaction with conventional oxidizing agents such as sodium or potassium metaperiodate followed by treatment with an alkali metal bicarbonate. The step (d) halogenation can be effected by contacting the compound with a metallic halide halogenating agent such as titanium tetrachloride, or stannic chloride preferably at lower than room temperature, e.g., about 0 to 4 degrees C.

The condensation reaction of the silylated or alkoxylated heterocyclic base with the 2-azido-2-deoxyarabinofuranosyl halide can be conducted in a conventional manner for condensing such bases with saccharide halides, for example as disclosed in British Patent Specification No. 1,070,413. Generally, the reaction is performed by simply mixing the two reactants in an aprotic solvent such as tetrahydrofuran, methylenechloride, 1,2-dichloroethane, benzene, and toluene. Use of a catalyst, such as tin tetrachloride, titanium tetrachloride, and mercury salts, is optional. The precise temperature and duration of the reaction are not critical and may be varied widely depending upon the reactants and solvents employed. However, high temperatures promote decomposition of the saccharide halide and are therefore not preferred. Generally, the reaction temperature can be varied between about 10 degrees and 80 degrees C. for 1 hr. to several days or weeks, with the longer times being used at the lower temperatures and with the less reactive heterocyclic bases.

To unblock the 3' and 5' oxygens of the 2-azido-2-deoxy arabinofuranosyl nucleosides described above requires a conventional saponification treatment, for example using methanolic sodium. Conversion of the resultant 3' and 5' hydroxyls to phosphate, sulfamate, phosphonate, or acyl groups can be accomplished by simply reacting the nucleoside with phosphoric, sulfamic or phosphorous acid or with hydrocarbon acids in the presence of condensing agents such as DCC or suitable derivatives of the acids such as halides or anhydrides. Further, the 5'-hydroxyl group can be replaced by halogenation with fluoro, chloro, bromo, or iodo atoms, or by replacement of these with an amino group.

Conversion of the 2'-azido group to an amino group can be accomplished by catalytic hydrogenation, for example using a nobel metal, such as platinum or palladium, catalyst.

Conversion of the amino group to a hydrocarbylamino group, such as an alkylamino or dialkylamino group wherein the alkyl substituents are methyl, ethyl, or propyl, can be accomplished by reacting the compound with a hydrocarbylhalide such as an alkylhalide, e.g., ethyl chloride, under conditions generally suitable for amine alkylation reactions. If monosubstitution is desired, it is preferred to first acylate the 2'-amino group.

Separation of the α and β anomers of the nucleosides and nucleotides of the present invention can be accomplished using conventional column chromatography and crystallization procedures.

The nucleosides and nucleotides of the present invention form acid addition salts with both organic and inorganic acids. Preferred acid addition salts are those which are pharmaceutically acceptable, such as the addition salts of hydrochloric acid, hydrobromic acid, sulfuric acid, phosphoric acid, citric acid, acetic acid, succinic acid, maleic acid, methanesulfonic acid, p-toluenesulfonic acid, and the like.

To use the nucleosides and nucleotides of the present invention, or their acid addition salts, as therapeutic agents for the treatment of mammals, it is preferred to formulate the particular compound in a dosage unit form comprising from about 1 to about 500 milligrams of the compound per kilogram of he average body weight of the mammal, per dosage unit. For example, the formulation may often contain about 100 to 2000 milligrams of the compound per dosage unit.

The active compound is preferably mixed or dissolved in a compatible pharmaceutical carrier such as, for example, water, gelatin, gum arabic, lactose, starches, magnesium stearate, talc, vegetable oils, polyalkylene glycols, petroleum jelly, etc. Administration of the compounds can be enteral or parenteral. Accordingly, their pharmaceutical preparations can either be in solid form (e.g., as tablets, capsules, dragees, or suppositories) or in liquid form (i.e., as solutions, suspensions, or emulsions). The preparations may be sterilized and/or may contain adjuvants such as preserving, stabilizing, wetting, or emulsifying agents, salts for varying the osmotic pressure, buffers, or other therapeutic agents.

The invention may be better understood by reference to the following, non-limiting examples.

EXAMPLE 1

Preparation of 5-O-Benzoyl-3-O-Acetyl-2-Azido-2-Deoxy-D-Arabinofuranosyl Chloride The following reaction sequence is accomplished in this example.

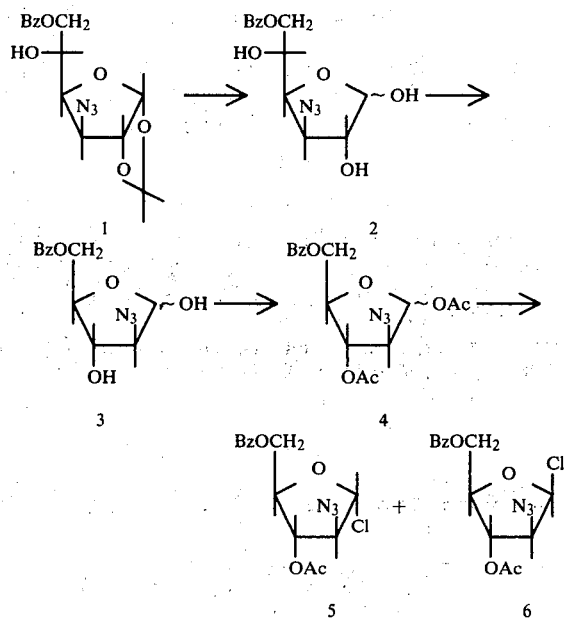

Benzoylation of 1,2-O-isopropylidene-3-azido-3-deoxy-α-D-glucofuranose with 1.05 molar equivalent of benzoyl chloride gives a greater than 90% yield of 1,2-O-isopropylidene-6-O-benzoyl-3-azido-3-deoxy-α-D-glucofuranose (1). A sample of 1 is purified on silica gel (CHCl$_3$-ether; 3:1), NMR (CDCl$_3$, TMS internal standard) δ 7.36–8.18 (2m, 5, aromatic), 5.93 (d, 1, J$_{1,2}$=3.5 Hz, H-1), 4.67 (d, 1, J$_{1,2}$=3.5 Hz, H-2), 4.25–4.80 (m, 5, H-3,4,5,6), 1.50, 1.33 (2s, 6, 2CH$_3$). Crude 1, which contains a small amount of 5,6-di-O-benzoate and a trace of 5-O-benzoate derivatives, is hydrolyzed in dioxane-water (1:1) with Dowex 50 [H$^+$] ion exchange resin to give 6-O-benzoyl-3-azido-3-deoxy-D-glucofuranose (2). Compound 2, which gives a poorly resolved NMR spectrum, is oxidized with sodium metaperiodate at 22–28 degrees C. for 3 hr., followed by treatment with NaHCO$_3$ (to hydrolyze the formyl group) overnight to give 5-O-benzoyl-2-azido-2-deoxy-D-arabinofuranose (3), which is purified by silica gel chromatography (CH$_2$Cl$_2$-ether; 3:1).

Compound 3 is acetylated with pyridine-acetic anhydride to give an anomeric mixture (α:β≈4:1, determined by NMR spectroscopy) of 1,3-di-O-acetyl-5-O-benzoyl-2-azido-2-deoxyarabinofuranose (4). For the α-anomer of 4, NMR (CDCl$_3$) δ 7.42–8.36 (2m, 5 aromatic), 6.20 (s,1, H-1), 5.14 (dd, 1, J$_{2,3}$=1.5 Hz, J$_{3,4}$=Hz, H-3), 4.20 (d,1,J$_{2,3}$=1.5 Hz, H-2); for the β-anomer of 4, δ 7.42–8.36 (2m, 5, aromatic), 6.39 (d,1,J$_{1,2}$=4.5 Hz, H-1), 5.56 (dd,1,J$_{2,3}$=8.0 Hz, J$_{4,3}$=6.0 Hz, H-3), 4.09 (dd,1,J$_{1,2}$=4.5 Hz, J$_{2,3}$=8.0 Hz, H-2).

Starting from 109 g. of 1,2-O-isopropylidene-3-azido-3-deoxy-α-D-glucofuranose, 86.4 g. of 4 (53.3% yield) is obtained. Compound 4 is converted to a mixture of 1-chloro derivatives 5 and 6 (5:6≈4:1) by treatment with TiCl$_4$ at 0–4 degrees C. for 3 hr. Compounds 5 and 6 are separated by silica gel chromatography (toluene-ethyl acetate, 8:1). For compound 5, NMR (CDCl$_3$), δ 7.32–8.20 (2m, 5H, aromatic), 6.13 (s,1,H-1), 5.10(d,1,J=4.5 Hz, H-3), 2.16 (s, 3H, Ac); 6 NMR (CDCl$_3$) δ 7.32–8.20 (2m, 5, aromatic), 6.25 (d,1,J$_{1,2}$=4.5 Hz, H-1), 5.65 (dd,1,J$_{2,3}$=8.5,J$_{3,4}$=6.0 Hz, H-3), 4.31 (dd,1,J$_{1,2}$=4.5 Hz, J$_{2,3}$=8.5 Hz, H-2), 2.13 (s,3H, Ac).

EXAMPLE 2

Preparation of 1-(2-Azido-2-Deoxy-3-O-Acetyl-5-O-Benzoyl-D-Arabinofuranosyl) Cytosine To a stirred solution of 7.8 g. of 2-azido-2-deoxy-3-O-acetyl-5-O-benzoyl-D-arabinofuranosyl chloride in 300 ml. of 1,2-dichloroethane is added 6 g. of bis(trimethylsilyl) cytosine dissolved in 200 ml. of 1-2-dichloroethane. The solution is stirred at 60–65 degrees C. for 3 days, cooled to room temperature and washed successively with 100 ml. of a saturated NaHCO$_3$ solution and 100 ml. of water. It is then dried and evaporated at reduced pressure at 45 degrees C., and the residue is dissolved in 50 ml. of chloroform. The chloroform solution is applied to a silica-gel column and the β and α anomers are eluted with an acetyl mixture of chloroform and 2-propanol (10:1). The β-anomer, 1-(2-azido-2-deoxy-3-O-acetyl-5-O-benzoyl-β-D-arabinofuranosyl) cytosine, is eluted from the column first, and is obtained after evaporation of the solvent in 37% yield. The α-anomer, 1-(2-azido-2-deoxy-3-O-benzoyl-α-D-arabinofuranosyl) cytosine, is obtained in 10% yield.

EXAMPLE 3

Preparation of 1-(2-Azido-2-Deoxy-$\beta$-D-Arabinofuranosyl) Cytosine ("Cytarazid")

To a stirred solution of 14 g. of 1-(2-azido-2-deoxy-3-O-acetyl-5-O-benzoyl-$\beta$-D-arabinofuranosyl) cytosine in 500 ml. of methanol is added a catalytic amount of sodium methoxide and the solution is stirred at room temperature overnight. The solution is evaporated to a syrup which is extracted twice with 200 ml. of ether. The residue is dissolved in 100 ml. of methanol and passed through a short column of Dowex 50 [NH$_4^+$] ion exchange resin. The column is washed with 500–1000 ml. of methanol and the methanol solution is evaporated to a syrup. The syrup is crystallized from ethanol to give 8.2 g. (85%) of 1-(2-azido-2-deoxy-$\beta$-D-arabinofuranosyl) cytosine, to which the trivial name cytarazid is assigned; $\lambda_{max}$ CH$_3$OH=273 nm, m.p. 157–158 (dec), NMR (DMSO-d$_6$, TMS) $\delta$ 7.76 (C$_6$H), 7.20 (NH$_2$), 6.17 (C$_1$,H), 5.75 (C$_5$H), 5.86 (O$_3$,H), 5.07 (O$_5$,H).

The $\alpha$-anomer, 1-(2-azido-2-deoxy-3-O-acetyl-5-O-benzoyl-$\alpha$-D-arabinofuranosyl) cytosine, is deblocked in the same manner; $\lambda_{max}$ CH$_3$OH=273 nm, m.p. 175–176(dec), NMR (DMSO-d$_6$, TMS) $\delta$ 7.68 (C$_6$H), 7.23 (NH$_2$), 5.76 (C$_1$,H), 5.82 (C$_5$H), 4.93 (O$_5$,H).

EXAMPLE 4

Preparation of 1-(2-Amino-2-Deoxy-$\beta$-D-Arabinofuranosyl) Cytosine ("Cytaramin")

To a solution of 1 g. of 1-(2-azido-2-deoxy-$\beta$-D-arabinofuranosyl) cytosine in 200 ml. of methanol is added a catalytic amount of PtO$_2$ and the mixture is hydrogenated at room temperature and atmospheric pressure for 1.5 hrs. The mixture is filtered through a Celite pad and the filtrate is evaporated to a syrup which is crystallized from methanol to give 820 mg. (91%) of 1-(2-amino-2-deoxy-$\beta$-D-arabinofuranosyl) cytosine, to which the trivial name cytaramin is assigned; $\lambda_{max}$ (NH$_2$)=276, m.p. 209, NMR (DMSO-d$_6$, TMS) $\delta$ 7.79 (C$_6$H), 7.03 (NH$_2$), 5.99 (C$_1$,H), 5.68 (C$_5$H).

EXAMPLES 5–10

Following the general condensation and deblocking procedures set forth in Examples 2 and 3 herein, but using the below-listed heterocyclic bases as reactants, in place of the silylated cytosine, the indicated arabinofuranosyl nucleosides are obtained:

| Example No. | Heterocyclic Base | Arabinofuranosyl Nucleoside |
|---|---|---|
| 5 | Bis (Trimethylsilyl) Uracil | 1-(2-Azido-2-Deoxy-D-Arabinofuranosyl) Uracil |
| 6 | Bis (Trimethylsilyl) Thymine | 1-(2-Azido-2-Deoxy-D-Arabinofuranosyl) Thymine |
| 7 | Bis (Trimethylsilyl)-5-Fluorouracil | 1-(2-Azido-2-Deoxy-D-Arabinofuranosyl)-5-Fluorouracil |
| 8 | Bis (Trimethylsilyl)-N-Benzoyl Adenine | 9-(2-Azido-2-Deoxy-D-Arabinofuranosyl) Adenine |
| 9 | Tris (Trimethylsilyl)-N-Acetyl Guanine | 9-(2-Azido-2-Deoxy -D-Arabinofuranosyl) Guanine |
| 10 | Trimethylsilyl-6-Chloropurine | 9-(2-Azido-2-Deoxy-D Arabinofuranosyl)-6-Chloro-purine |

EXAMPLE 11

A portion of each of the anomers of the arabinofuranosyl nucleosides prepared in Examples 5–10 is converted to its 2'-amino counterpart by the catalytic hydrogenation procedure set forth in Example 4 herein.

EXAMPLE 12

In Vitro Cytotoxicity Testing

Cytarazid, the $\beta$-anomer of the nucleoside prepared in Example 3 herein, and cytaramin, the nucleoside prepared in Example 4 herein, are evaluated in vitro for growth inhibiting potency against mammalian cancer cells by a micro technique, using the culture conditions described by Bobek et al. in *J. Med. Chem.*, vol. 20, p. 458 (1977), whereby 0.5 ml. aliquots of medium (RPMI 1640÷10% fetal calf serum) containing the test compound are introduced into 16×125 mm. screw cap culture tubes, followed by 0.5 ml. portions of the medium containing 1×10$^5$ mammalian cancer cells. The cultures are incubated at 37 degrees C. for 40 hr., after which time the viable cells are counted by Trypan Blue exclusion. During this time the cell number in the controls increases about four to nine-fold with an average cell viability of 99%. The test results are as follows:

| Cell Line | Concentration for 50% Inhibition of Growth | |
|---|---|---|
|  | Cytarazid | Cytaramin |
| HeLa | 2 × 10$^{-7}$ | 3 × 10$^{-5}$ |
| Molt 4F (T-type from lymphoblastic leukemia) | 7 × 10$^{-8}$ | N.T. |
| L-1210 | 6 × 10$^{-7}$ | 4 × 10$^{-6}$ |

When subjected to this same cytotoxicity test, the uracil derivative counterparts of cytarazid and cytaramin exhibited no growth inhibiting potency.

EXAMPLE 13

In Vivo Cytotoxicity Testing

Cytarazid and cytaramin are evaluated in vivo for growth inhibitory potency against leukemic cells by intraperitoneally inoculating DBA/2 HaDD mice with an IP-PBS saline suspension of 1×10$^6$ L-1210 leukemic cells, waiting 24 hrs., and then administering the test compound intraperitoneally in 0.2 ml. of saline-phosphate buffer solution (pH 7.0).

| Compound | Dosage | No. of Mice | Survival Time (days) |
|---|---|---|---|
| Control |  | 4 groups 6 mice/group | 8.7 |
| Cytarazid | 40 mg/kg administered twice per day 8 hrs. apart for 2 days beginning 24 hrs. after tumor inoculation | 4 groups 6 mice/group | >120 |
| Cytaramin | 75 mg/kg administered twice per day 8 hrs. apart for 2 days beginning 24 hrs. after | 4 groups 6 mice/group | >120 |

| Compound | Dosage | No. of Mice | Survival Time (days) |
|---|---|---|---|
| | tumor inoculation | | 5 |

EXAMPLE 14

Enzymatic Deamination Resistance Testing

Partially purified CR-CdR deaminase is prepared from two different sources: (1) human liver, following the procedure of Wentworth and Wolfender, *Biochemistry*, vol. 14, p. 5099 (1975), and (2) blast cells of patients with acute myelocytic leukemia, using ammonium sulfate fractionation and DEAE column chromatography. The assay procedure is described by Wentworth and Wolfander, ibid. Under these conditions 50% of the commercially available anti-tumor agent, cytarabine, is deaminated in 45 minutes, whereas no significant deamination of cytaramin or cytarazid is detected in 8 hrs.

EXAMPLE 15

In Vitro Antimicrobial Testing

Cytarazid and cytaramin both prove effective to prevent the growth of *E. coli* and *S. faecium* at concentrations of about 0.08 to 1.5 μM, when evaluated by the following assay procedure, which is described in greater detail by Bobek et al. in *J. Med. Chem.*, vol. 13, p. 411 (1970):

*S. faecalis* is grown in the medium of Flynn et al. (1951) from which uracil and the purines are omitted, and to which 1 mμg/ml of folic acid is added. *E. coli* is grown in the synthetic medium described by Gray and Tatum (1944). The assays are carried out by placing 1 ml. portions of the media into 13×100 mm Pyrex culture tubes and adding 1 ml of water or of the solution containing the test compound. Sterilization is carried out by autoclaving or filtration.

The inocula are prepared from cultures of the test organisms grown in 5 ml of the basal medium for 20 hr. at 37 degrees C. Following centrifugation and washing twice with isotonic saline, the cells are resuspended in enough saline to yield an optical density of 0.30 at 470 mμ as measured in a Beckman Model B spectrophotometer. A 1 ml. portion of this suspension containing approximately $1.5 \times 10^7$ cells is diluted tenfold in saline, and 1 drop of this final dilution is placed in each assay tube. Incubation proceeds for 20 hrs. at 37 degrees C. All *E. coli* assays are carried out by shaking the cultures during incubation. The extent of growth is determined by means of a Klett-Summerson photoelectric colorimeter using a red filter (640–700 mμ).

EXAMPLE 16

In Vitro Antiviral Testing

Cytarazid and cytaramin, when tested in vitro against Herpes Simplex types I and II viruses, utilizing the plaque reduction technique described by Dulbecco, *Proceedings National Academy of Sciences*, vol. 38, p. 747, exhibit significant antiviral properties. Cytarazid, for example, when used at 50 μM concentration against Herpes Simplex type I, inhibited in excess of 99.9% (3 log) of the virus and when used against type II inhibited greater than 99% (2 log).

We claim:

1. A compound selected from the group consisting of arabinofuranosyl nucleosides of the formula

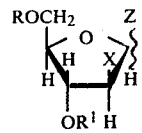

wherein Z is a pyrimidinyl-1 or purinyl-9 moiety, X is selected from the group consisting of amino, azido, and hydrocarbylamino of 1 to 7 carbon atoms, and each of R and $R^1$ is selected from the group consisting of hydrogen, acetyl, propionyl, butyryl, valeryl, isovaleryl, hexanoyl, heptanoyl, octanoyl, nonanoyl, undecanoyl, lauroyl, benzoyl, phenylacetyl, phenylpropionyl, o-, m-, and p-methylbenzoyl, β-cyclopentylpropionyl, and dihydrocinnamoyl, and acid addition salts thereof.

2. A compound selected from the group consisting of 1-(2-amino-2-deoxy-β-D-arabinofuranosyl)cytosine of the formula:

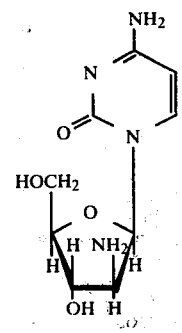

and pharmaceutically acceptable acid addition salts thereof.

3. A compound selected from the group consisting of 1-(2-azido-2-deoxy-β-D-arabinofuranosyl)cytosine of the formula:

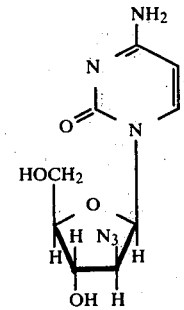

and pharmaceutically acceptable acid addition salts thereof.

4. The compound of claim 1 wherein X is amino or azido.

5. The compound of claim 1 wherein X is amido, R is hydrogen or benzoyl, and $R^1$ is hydrogen or acetyl.

6. The compound of claim 1 wherein X is amino or azido, each of R and $R^1$ is hydrogen, and the acid addition salts are pharmaceutically acceptable acid addition salts.

7. The compound of any of claims 4, 5, or 6 wherein Z is a pyrimidinyl-1 moiety from a pyrimidine base of the formula

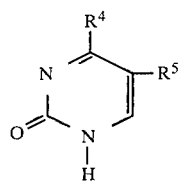

wherein $R^4$ is amino, hydroxy, thio, hydroxylamino, alkylamino, arylamino, or aralkylamino, and $R^5$ is fluoro, bromo, chloro, hydrogen, iodo, mercapto, nitro, nitrilo, thiocyanato, alkyl, alkenyl, or alkynyl.

8. The compound of any of claims 4, 5, or 6 wherein Z is a purinyl-9 moiety from a purine base of the formula

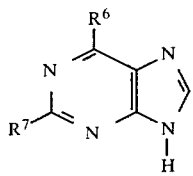

wherein $R^6$ is amino, hydrogen, hydroxylamino, thio, chloro, alkylamino, arylamino, or aralkylamino, and $R^7$ is hydrogen, oxo, chloro, fluoro, amino, nitro, thio, or hydroxyalkyl.

9. The compound of any of claims 4, 5, or 6 wherein Z is selected from the group consisting of uracilyl-1, thyminyl-1, 5-fluorouracilyl-1, adeninyl-9, guaninyl-9, and 6-chloropurinyl-9.

10. A composition in dosage unit form comprising an arabinofuranosyl nucleoside of the formula

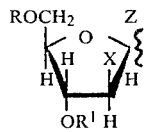

wherein Z is a pyrimidinyl-1 or purinyl-9 moiety, X is selected from the group consisting of amino, azido, and hydrocarbylamino of 1 to 7 carbon atoms, and each of R and $R^1$ is selected from the group consisting of hydrogen, acetyl, propionyl, butyryl, valeryl, isovaleryl, hexanoyl, heptanoyl, octanoyl, nonanoyl, undecanoyl, lauroyl, benzoyl, phenylacetyl, phenylpropionyl, o-, m-, and p-methylbenzoyl, β-cyclopentylpropionyl, and dihydrocinnamoyl, said nucleoside being either in the free base form or in the form of a pharmaceutically acceptable acid addition salt, and a sterile, compatible, pharmaceutical carrier for said nucleoside.

11. The composition of claim 10 wherein the arabinofuranosyl nucleoside is a compound selected from the group consisting of 1-(2-amino-2-deoxy-β-D-arabinofuranosyl) cytosine of the formula:

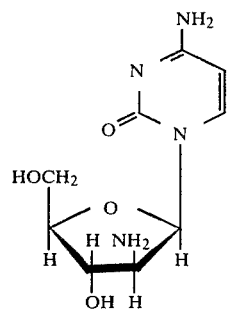

and pharmaceutically acceptable acid addition salts thereof.

12. The composition of claim 10 wherein the arabinofuranosyl nucleoside is a compound selected from the group consisting of 1-(2-azido-2-deoxy-β-D-arabinofuranosyl) cytosine of the formula:

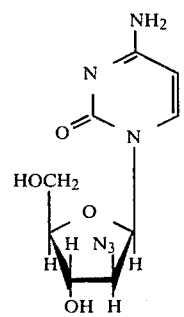

and pharmaceutically acceptable acid addition salts thereof.

* * * * *